(12) United States Patent
Tichauer (10) Patent No.: US 8,747,328 B2
(45) Date of Patent: Jun. 10, 2014

(54) CONTINUOUS BLOOD PRESSURE MONITORING

(75) Inventor: Larry M. Tichauer, La Palma, CA (US)

(73) Assignee: Raytheon BBN Technologies Corp., Cambridge, MA (US)

( * ) Notice: Subject to any disclaimer, the term of this patent is extended or adjusted under 35 U.S.C. 154(b) by 427 days.

(21) Appl. No.: 13/097,994

(22) Filed: Apr. 29, 2011

(65) Prior Publication Data

US 2012/0277602 A1 Nov. 1, 2012

(51) Int. Cl.
*A61B 5/02* (2006.01)

(52) U.S. Cl.
USPC .......................................... 600/494; 600/485

(58) Field of Classification Search
USPC ........................................................ 600/494
See application file for complete search history.

(56) References Cited

U.S. PATENT DOCUMENTS

| | | | |
|---|---|---|---|
| 4,592,365 A | 6/1986 | Georgi | |
| 4,677,984 A | 7/1987 | Sramek | |
| 4,889,132 A | 12/1989 | Hutcheson et al. | |
| 5,027,641 A | 7/1991 | Costello, Jr. | |
| 5,101,828 A | 4/1992 | Welkowitz et al. | |
| 5,392,781 A | 2/1995 | Phillipps et al. | |
| 5,564,426 A | 10/1996 | Iwai | |
| 5,642,734 A | 7/1997 | Ruben et al. | |
| 5,752,920 A * | 5/1998 | Ogura et al. | 600/494 |
| 5,772,600 A | 6/1998 | Kahn et al. | |
| 5,803,911 A | 9/1998 | Inukai et al. | |
| 5,913,826 A | 6/1999 | Blank | |
| 6,027,452 A | 2/2000 | Flaherty et al. | |
| 6,258,037 B1 | 7/2001 | Dowling, Jr. | |
| 6,517,495 B1 | 2/2003 | Hersh | |
| 6,647,287 B1 | 11/2003 | Peel, III et al. | |
| 6,767,328 B2 | 7/2004 | Kulik | |
| 6,918,879 B2 | 7/2005 | Ting et al. | |
| 7,029,448 B2 | 4/2006 | Kubo | |
| 7,192,403 B2 | 3/2007 | Russell | |
| 7,260,431 B2 | 8/2007 | Libbus et al. | |
| 7,341,560 B2 * | 3/2008 | Henderson et al. | 600/500 |
| 7,587,238 B2 | 9/2009 | Moffitt et al. | |
| 7,601,123 B2 | 10/2009 | Tweed et al. | |
| 7,725,187 B1 * | 5/2010 | Nabutovsky et al. | 607/19 |
| 7,805,193 B2 | 9/2010 | Libbus et al. | |
| 7,822,299 B2 | 10/2010 | Borgos et al. | |
| 8,043,223 B2 * | 10/2011 | Friedman et al. | 600/485 |
| 2002/0099296 A1 * | 7/2002 | Flaherty et al. | 600/485 |
| 2003/0004421 A1 | 1/2003 | Ting et al. | |
| 2003/0032869 A1 | 2/2003 | Muramatsu et al. | |
| 2003/0045909 A1 | 3/2003 | Gross et al. | |
| 2004/0024323 A1 | 2/2004 | Kulik | |
| 2004/0147969 A1 | 7/2004 | Mann et al. | |
| 2005/0070805 A1 | 3/2005 | Dafni | |
| 2005/0075531 A1 | 4/2005 | Loeb et al. | |
| 2005/0119578 A1 * | 6/2005 | Kubo | 600/490 |

(Continued)

*Primary Examiner* — Michael Kahelin
*Assistant Examiner* — Mitchell Alter
(74) *Attorney, Agent, or Firm* — Ropes & Gray LLP (57) ABSTRACT

The systems and methods monitor a subject's blood pressure under a constant applied pressure. Measurements taken from a pressure measuring element and a pulse sensing element are combined to determine the subject's systolic and diastolic pressure. The systolic pressure is measured directly by the pressure measuring element, and the diastolic pressure is determined indirectly by using a pulse waveform to extrapolate portions of a pressure waveform. The systems and methods can be employed in any number of applications, including, without limitation, taking a single reading from a subject, continuously monitoring a subject, or evaluating a subject during physical exertion.

38 Claims, 8 Drawing Sheets

(56) References Cited

U.S. PATENT DOCUMENTS

| | | |
|---|---|---|
| 2005/0261741 A1 | 11/2005 | Libbus et al. |
| 2006/0206031 A1 | 9/2006 | Hasegawa |
| 2006/0206154 A1 | 9/2006 | Moffitt et al. |
| 2006/0229488 A1 | 10/2006 | Ayre et al. |
| 2006/0264771 A1 | 11/2006 | Lin et al. |
| 2007/0032729 A1 | 2/2007 | Fortin |
| 2007/0135717 A1 | 6/2007 | Uenishi et al. |
| 2007/0276265 A1 | 11/2007 | Borgos |
| 2007/0287927 A1 | 12/2007 | Borgos |
| 2008/0015648 A1 | 1/2008 | Libbus et al. |
| 2008/0071180 A1 | 3/2008 | Borgos |
| 2008/0118901 A1 | 5/2008 | Morris |
| 2008/0183053 A1 | 7/2008 | Borgos et al. |
| 2008/0255463 A1 | 10/2008 | Chowienczyk et al. |
| 2009/0036938 A1 | 2/2009 | Shipley et al. |
| 2009/0076423 A1 | 3/2009 | Reeves et al. |
| 2010/0063405 A1 | 3/2010 | Kashif et al. |
| 2010/0210957 A1 | 8/2010 | Inoue et al. |
| 2010/0249616 A1 | 9/2010 | Donehoo et al. |

\* cited by examiner

CONTINUOUS BLOOD PRESSURE MONITORING

TECHNICAL FIELD

The systems and methods described herein relate to measuring a physiological parameter, and is particularly suitable for continuous monitoring of blood pressure.

BACKGROUND

Blood pressure is a vital physiological measurement often used to assess the health and condition of an individual. A patient may be prescribed special medication or encouraged to take up an exercise regimen if blood pressure readings are higher than normal values defined based on the patient's age, weight, sex, or other characteristics. In addition, blood pressure readings may also be used to identify patients at risk of kidney failure, stroke, heart attack, or other serious, potentially life-threatening medical risks. Accordingly, blood pressure is a vital measurement and accurate blood pressure readings are critical to assessing a patient's health.

The standard method of obtaining blood pressure measurements uses pressure typically applied at a patient's bicep to determine the patient's diastolic and systolic blood pressure. A sphygmomanometer, which includes an inflatable cuff with a manometer to read pressure, is placed around a patient's arm and the inflatable cuff is inflated to apply a pressure to the patient's arm that is sufficient to occlude the patient's blood vessels. A medical practitioner uses a stethoscope to listen for the patient's pulse at a location on the arm distal from the cuff. When the vessels are occluded, no pulse is present and the practitioner hears no sounds. A release valve in the cuff is then opened, gradually releasing air from the cuff and decreasing the applied pressure. When the pressure in the cuff falls below the patient's systolic blood pressure, circulation in the arm begins as the vessels are no longer occluded. The circulation causes an audible heartbeat sounds, commonly referred to as Korotkoff sounds, that are detectable by the medical practitioner. The pressure in the cuff at the time these sounds begin is marked as the systolic pressure. The air in the cuff is then released until the pulse sounds are no longer audible, and the pressure in the cuff at which the pulse sounds disappear is recorded as the patient's diastolic blood pressure.

When a patient's blood pressure is measured, the pressure suddenly applied to the arm alerts the patient that a reading is being taken. Especially for patients who regularly experience a level of anxiety during clinical visits, this may trigger an involuntary increase in the patient's heart rate or tensing of the patient's muscles. The elevated stress level of the patient may cause inaccurate blood pressure measurements that are artificially increased by the patient's anxiety. This phenomenon is commonly referred to as the white coat effect, and can lead to improper diagnoses of hypertension. The increased pressure applied to the patient's arm, which is necessary for traditional blood pressure measurement, may thus serve as a stimulus for artificial increased blood pressure and inaccurate measurements.

Standard blood pressure measurements also create problems in obtaining consecutive blood pressure readings from a patient. When the inflatable cuff is inflated to occlude the blood vessels, the vessels and the patient's tissue are place under a high degree of compression. Due to inelastic properties of the vessels and tissue, this compression is not immediately relieved when the cuff is removed from the patient. Thus, a subsequent blood pressure reading taking immediately after a first reading is not reliable, as errors are introduced by the partial compression of the patient's tissue. A second reading can be accurately obtained from the patient's second arm, but this is inconvenient and still creates problems for readings beyond the second measurement.

SUMMARY

Accordingly, systems and methods for measuring a patient's blood pressure without alarming the patient at the time a measurement is taken are desirable. It is also desirable to allow for continuous, consecutive blood pressure measurements to be taken without introducing error caused by tissue compression.

The systems and methods described continuously measure a subject's blood pressure. For ease of description and simplicity, these systems and methods will be described for the specific application of continuously measuring a subject's blood pressure by comparing measurements taken from two sensors, a pressure sensor and a pulse sensor, applied to the subject. However, embodiments can be employed to utilize other sensors, such as heart rate or electrocardiogram sensors, and to measure other physiological parameters, and the sensors employed and parameters measured will vary according to the application being addressed.

The systems and methods described herein continuously monitor a subject's blood pressure. In one embodiment, two sensors obtain physiological measurements from the subject. A first sensor obtains pressure measurements, and a second sensor monitors the subject's pulse waveform. Readings obtained from the two sensors are combined to create a comprehensive representation of the subject's blood pressure trend. The combined data is then used to continuously determine the subject's diastolic and systolic blood pressures.

According to one embodiment, a pressure sensor applies a constant pressure to a subject and measures the subject's blood pressures that exceed the constant pressure. The constant pressure is chosen such that it is within a range greater than the subject's diastolic pressure and lower than the subject's systolic pressure. The constant pressure allows for continuous blood pressure measurement and does not alert the subject that a reading is being taken with a sudden increase in pressure that can lead to complications due to the white coat effect. The pressure applied is also low enough that error caused by tissue compression is avoided.

According to one embodiment, blood pressures that are below the constant applied pressure are masked by the applied pressure and, thus, are not measured directly using the pressure sensor. A waveform obtained from the pulse sensor has substantially the same shape as the pressure waveform and can be used to estimate the masked pressures. Measurements taken from the pulse sensor are used to extrapolate the masked portions of the pressure wave such that the masked pressures, most notably the subject's diastolic pressure, can be determined. The pressure and pulse waveforms are typically normalized before they are combined to minimize any scaling differences between the two waveforms. The normalized waveforms are aligned and overlaid. The waveforms may be aligned using landmarks, such as the systolic peak or dicrotic notch, that are present within both waveforms. A normalized pulse waveform may be overlaid with a normalized pressure waveform, and portions of the pulse waveform are used to extrapolate points in the pressure waveform corresponding to pressures that are masked by the applied pressure and are not directly measured. A completed pressure waveform, including directly measured portions and portions extrapolated from a pulse waveform, is restored to the scale of an original pressure waveform to create a complete representation of the subject's blood pressure trend. The restored trend may be used to determine the subject's systolic and diastolic blood pressures.

Optionally, periodic calibration is used to maintain the accuracy of measurements obtained. The calibrations may be used to test for nonlinearities or irregularities in pressure data, or to determine an optimal pressure to use as a constant applied pressure. The calibrations may be performed automatically at set intervals or may be performed in response to user control. The frequency of automatic calibrations may be dynamically adjusted based on the stability and reliability of past pressure readings.

BRIEF DESCRIPTION OF THE DRAWINGS

The foregoing and other objects and advantages of the invention will be appreciated more fully from the following further description thereof, with reference to the accompanying drawings. These depicted embodiments are to be understood as illustrative of the invention and not as limiting in any way.

DETAILED DESCRIPTION

To provide an overall understanding of the invention, certain illustrative embodiments will now be described, including systems and methods for continuous measurement of blood pressure. It will be understood by one of ordinary skill in the art that the systems and methods described herein may be adapted and modified as is appropriate, and that the systems and methods described herein may be employed in other suitable applications, and that such other additions and modifications will not depart from the scope hereof.

The systems and methods described herein utilize measurements from two physiological sensors to continuously derive measurements of a subject's systolic and diastolic blood pressures. A first sensor applies a constant pressure at a location on the subject that blood pressure can be accurately measured and measures pressures incident on the sensor that are caused by blood flow in the subject's tissue at that location. A second sensor is applied either at a different location or at the same location on the subject as the first sensor and monitors the subject's pulse. For each pulse, the subject's systolic blood pressure is measured directly by the first sensor, and the subject's diastolic blood pressure is determined by combining and processing measurements from both the first and second sensors. Measurements from the two sensors are combined to extrapolate portions of the monitored pressure waveform that are not directly measured by the first sensor.

Figure 1:
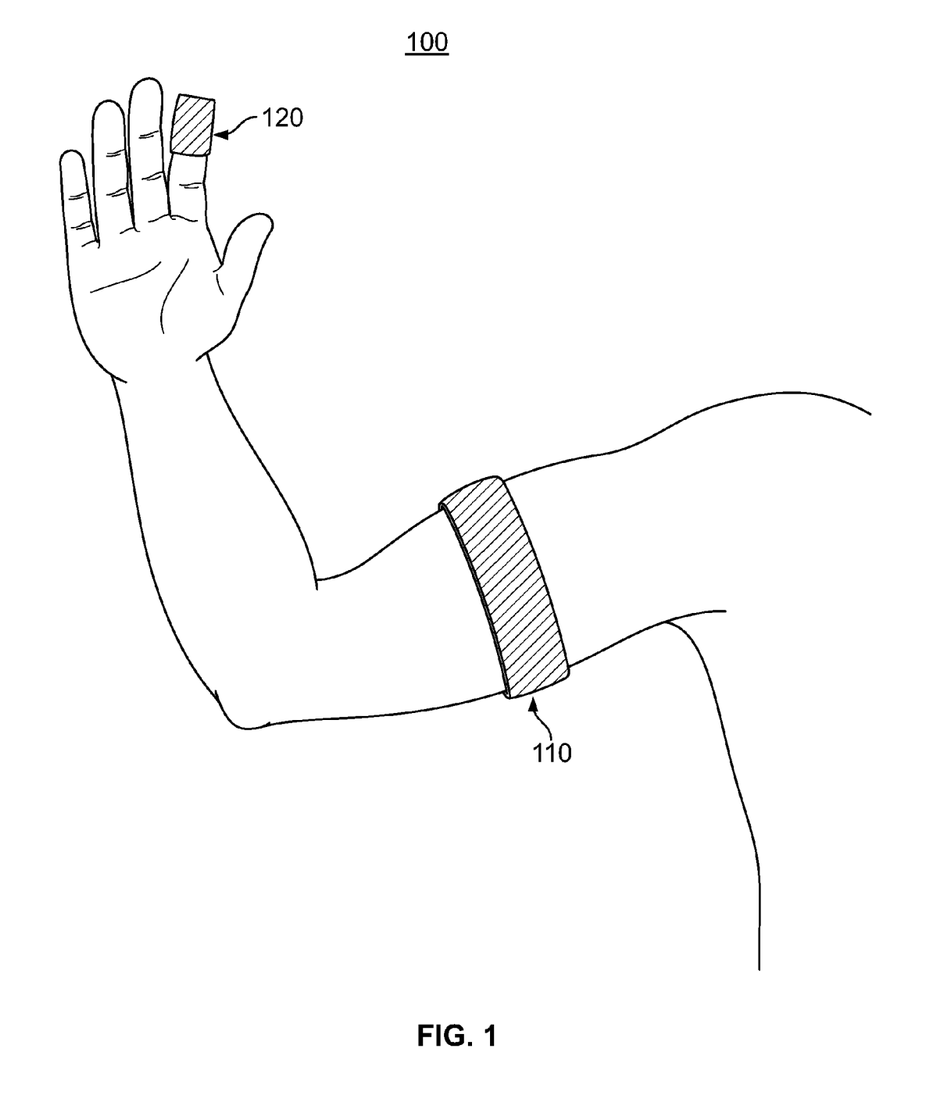
FIG. 1 shows a conceptual view of an illustrative measurement system.

FIG. 1 shows a measurement system 100 including two measuring elements, a pressure sensor 110 and a pulse sensor 120, applied to a subject. In FIG. 1, pressure sensor 110 is located on a subject's bicep, and pulse sensor 120 is located on a finger on the same arm of the subject. It will be understood by one of ordinary skill in the art, however, that these sensors may be located on opposite arms, or on areas of the subject other than the arm. As with conventional blood pressure measuring techniques, it may be preferable to locate pressure sensor 110 at a location at the same height as a subject's heart, such as the upper arm, to minimize gravitational effects and transient pressure differences. In some embodiments, however, pressure sensor 110 may be located in any other location on a subject that reliable pressure readings can be obtained. Different locations may require data correction to account for transient pressure differences if pressure sensor 110 is not located level with the subject's heart. Pulse sensor 120 may be located at any location on a subject at which reliable pulse measurements can be obtained.

Pressure sensor 110, which may be, for example, a sphygmomanometer, monitors a pressure waveform that is indicative of the subject's blood pressure. The pressure waveform is monitored by applying a constant pressure to the subject's arm using pressure sensor 110 and continuously measuring the pressure incident on pressure sensor 110 from the patient's arm. The pressure incident on pressure sensor 110 is caused by blood circulating through the subject's arm, and the amount of the incident pressure increases and decreases as the subject's blood pressure rises and falls within each cardiac cycle. The detected pressure is created when the subject's blood pressure is higher than the applied constant pressure and overcomes the applied pressure to create an additional incident pressure on pressure sensor 110. When the subject's blood pressure is lower than the applied constant pressure, there is not sufficient pressure to create this additional incident pressure, and pressure sensor 110 detects only the constant pressure. The subject's actual blood pressure during this time is thus masked by the pressure applied by pressure sensor 110.

Suitable measuring elements that can be used as pressure sensor 110 include sphygmomanometers with integrated pressure sensors, other inflatable cuffs capable of measuring incident pressures, a band with an integrated pressure sensor and pressure applying element, an optical sensor integrated with a pressure applying element, or any other devices suitable for applying pressure to a subject and measuring an incident pressure. In some embodiments, pressure sensor 110 may be integrated into clothing worn by the subject, for example, in the arm of a shirt or in an undergarment. The clothing with the integrated sensor may be programmable so that the pressure applied by the integrated sensor can be continually adjusted. Pressure sensor 110 may apply a constant pressure uniformly around the circumference of the subject's limb, or the applied constant pressure may be localized to only a portion of the circumference of the subject's limb. For example, in measurement system 100, pressure sensor 110 may apply pressure localized on the inner portion of the subject's arm to direct the pressure at the brachial artery that runs along the inside of the subject's arm. Directing the applied pressure at an arterial vessel may increase the accuracy and resolution of pressure measurements taken with a pressure measuring element. If the applied pressure is localized, it may be advantageous to place the sensor measuring pressure incident on the measuring element at the same location.

Pulse sensor 120, which may be, for example, a pulse oximeter, is configured to measure light transmission or reflection to monitor a pulse waveform indicative of the volume of blood pulsing through the subject's tissue. Suitable measuring elements that can be used as pulse sensor 120 are a pulse oximeter, ultrasound sensor, aural sensor, potentiometer, diaphragm contacting the skin and creating a signal based on motion of the diaphragm, or any other devices suitable for measuring a subject's pulse.

During subject monitoring, pressure readings taken by pressure sensor 110 and the pulse waveform monitored by pulse sensor 120 are combined to determine the subject's systolic and diastolic blood pressures. In an embodiment, the constant pressure applied to the subject by pressure sensor 110 is set to a pressure determined to be less than the subject's systolic pressure but greater than the subject's diastolic pressure. The constant pressure may also be set to be less than the pressure at the dicrotic notch, as is discussed in more detail below with respect to FIG. 3. Applying a constant pressure that does not exceed the systolic pressure allows for continuous blood pressure readings to be taken while avoiding, or reducing, errors caused by the white coat effect or inelasticity of the subject's blood vessels. The subject feels only a constant pressure and not a sudden increase in pressure like that used in conventional techniques, and, thus, there is no trigger that alerts the subject that a measurement is being taken and causes the subject to tense up at the time of measurement. Additionally, the applied constant pressure, which may be, for example, in the range 80-100 mmHg, is less than the pressure required for traditional blood pressure measurements, which is greater than the systolic pressure and is typically in the range 120-140 mmHg. Thus, the applied constant pressure, in contrast to the pressure applied for traditional measurements, does not occlude the blood vessels completely or compress the subject's tissue and vessels to a degree that the inelastic properties of the vessels introduce error into consecutive measurements.

Because pressure sensor 110 measures pressures incident on the sensor, pressure that are lower than the applied constant pressure, namely the diastolic pressure, are masked by the applied pressure and are not measured directly by pressure sensor 110. The pulse waveform monitored by pulse sensor 120, which has a shape that highly correlates to the pressure waveform, can be used to extrapolate the masked portions of the patient's blood pressure trend. Thus, the subject's systolic blood pressure, which is greater than the applied pressure, is measured directly by pressure sensor 110, and the subject's diastolic pressure is determined indirectly by extrapolating the masked portion of the subject's pressure waveform using the pulse waveform from pulse sensor 120.

Figure 2:
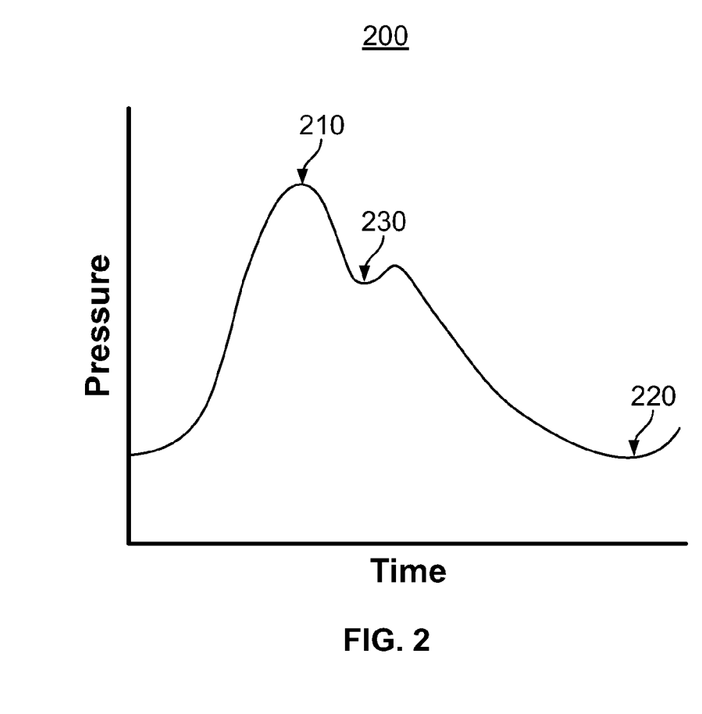
FIG. 2 shows an illustrative graph of a blood pressure waveform.

FIG. 2 shows a typical subject's blood pressure waveform 200 for a single cardiac pulse. As the heart contracts to eject blood during a single cardiac cycle, a subject's blood pressure increases to systolic pressure 210, the maximum pressure during the pulse. The blood pressure then falls as the heart relaxes and fills with blood for a subsequent pulse, and the pressure reaches the diastolic pressure 220, the lowest pressure during the pulse, before the heart begins to contract again for a subsequent cardiac cycle.

In addition to the systolic and diastolic pressures in the pulse waveform, the dicrotic notch 230 is a distinguishable landmark generally present within each pulse. The dicrotic notch 230 is a small dip in the pressure waveform that marks the transition from systole, or ventricular contraction of the heart, to diastole, or ventricular relaxation. The pronounced dip results from a transient increase in aortic pressure following the closure of heart valves during each cardiac cycle and is present at generally the same temporal location relative to the systolic and diastolic pressures in each pulse. As is discussed further below, the systolic pressure 210, diastolic pressure 220, and dicrotic notch 230 correspond to analogous points in a typical pulse waveform and can be useful landmarks for aligning a pressure waveform for a pulse or series of pulses with a corresponding pulse waveform, as is discussed in more detail below.

A constant pressure applied to a subject's limb, such as the pressure applied by pressure sensor 110 discussed above in relation to FIG. 1, is used in a typical embodiment to allow for continuous monitoring of the subject's systolic and diastolic pressures. The applied pressure can be selected from the range of pressures between the subject's systolic and diastolic pressures. By using a pressure in this range, a high degree of accuracy in directly measuring the systolic pressure may be achieved while maintaining the applied pressure at a level that will not greatly compress the subject's vessels and, thus, avoids inaccuracies that can be caused by the inelastic characteristics of the vessels.

Figure 3:
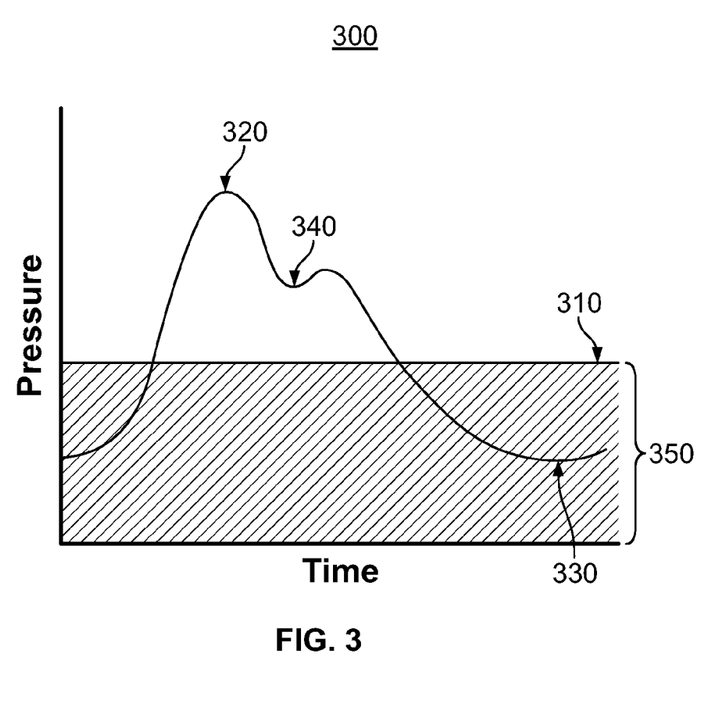
FIG. 3 shows an illustrative graph of a blood pressure waveform and an applied constant pressure.

FIG. 3 shows a constant pressure 310 applied to a subject in relation to the subject's blood pressure waveform 300 according to an embodiment of the invention. The applied pressure 310 is selected such that it is greater than the subject's diastolic pressure 330 but less than the subject's systolic pressure 320 and the pressure at the dicrotic notch 340. In an embodiment, the applied pressure may be selected based on previous measurements of a subject's blood pressure. For example, the applied pressure may be set as a percentage of the subject's most recent measured systolic blood pressure. The applied pressure may also be determined as a function of the subject's systolic pressure, diastolic pressure, dicrotic pressure, or any suitable combination thereof.

A pressure sensor used to create applied pressure 310, such as pressure sensor 110 discussed above in relation to FIG. 1, measures pressure incident on the sensor. Because the subject's systolic pressure 320 is greater than the applied pressure 310, the systolic pressure will create a pressure incident on the pressure sensor. The magnitude of the incident pressure is directly correlated to the difference between the systolic pressure 320 and the applied pressure 310. Thus, the pressure reading taken from the measuring element can be used to directly measure the subject's systolic pressure 320 during each cardiac cycle. Depending on the pressure sensor technique employed, the pressure sensor output may be a reading of the full systolic pressure or may only be a reading of the portion of the systolic pressure that exceeds the applied pressure, which can be added to the known applied pressure to obtain the full systolic pressure.

A subject's blood pressures during a cardiac cycle that fall below applied pressure 310, however, are masked by the applied pressure and cannot be measured directly. When the blood pressure is less than applied pressure 310, there is not sufficient pressure in the subject's limb to overcome the applied pressure, and there is no additional pressure incident on the measuring element. Thus, any portions of the subject's blood pressure waveform during which the pressure is less than applied pressure 310, such as when the blood pressure is within pressure range 350, are masked by applied pressure 310 and cannot be directly measured by the measuring element. Instead, these portions of the cardiac cycle create constant pressure readings equal to either applied pressure 310 or zero pressure, depending on the pressure sensor technique used. In the embodiment shown in FIG. 3, the subject's diastolic pressure 330 falls within pressure range 350, and thus the diastolic pressure is not measured directly using only the pressure-sensing measuring element when applied pressure 310 is used.

Figure 4:
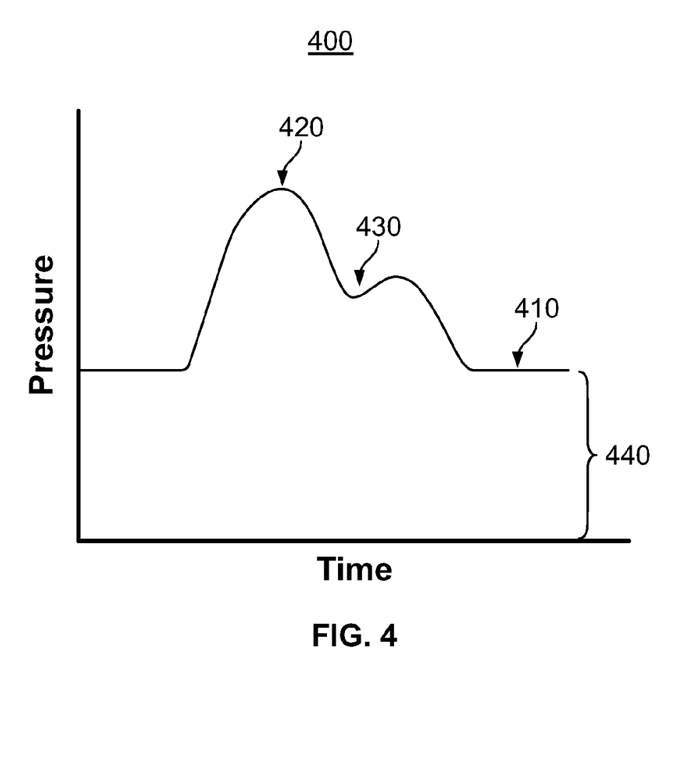
FIG. 4 shows an illustrative measured pressure waveform.

The pressure waveform 400 measured by a measuring element during the application of a constant pressure to a subject's limb is shown in FIG. 4. As is shown in FIG. 4, the portions of the cardiac cycle during which the subject's blood pressure is below the applied pressure are read by the measuring element as a constant pressure 410, which is equal to the applied pressure. During the portions of the cardiac cycle for which the subject's blood pressure is above the applied pressure, however, a measurable incident pressure is created on the measuring element. Thus, these portions of the cardiac cycle, which include systolic pressure 420 and the pressure at the dicrotic notch 430, are directly measured by the measuring element. As was discussed above in relation to FIG. 3, the portions of the cardiac cycle during which the blood pressure is below applied pressure are masked by the applied pressure, and these pressures in pressure range 440, including the subject's diastolic pressure, are not measured directly.

Two notable landmarks, the systolic pressure 420 and pressure at the dicrotic notch 430, are directly measured and discernible in waveform 400. The temporal position of these landmarks relative to other portions of the waveform is generally consistent over multiple pulses. Thus, these two measured landmarks are useful for aligning and comparing pulses or, as is discussed in more detail below with respect to FIG. 7, for aligning a pulse from pressure waveform 400 with a similarly-shaped pulse from a pulse waveform.

Figure 5:
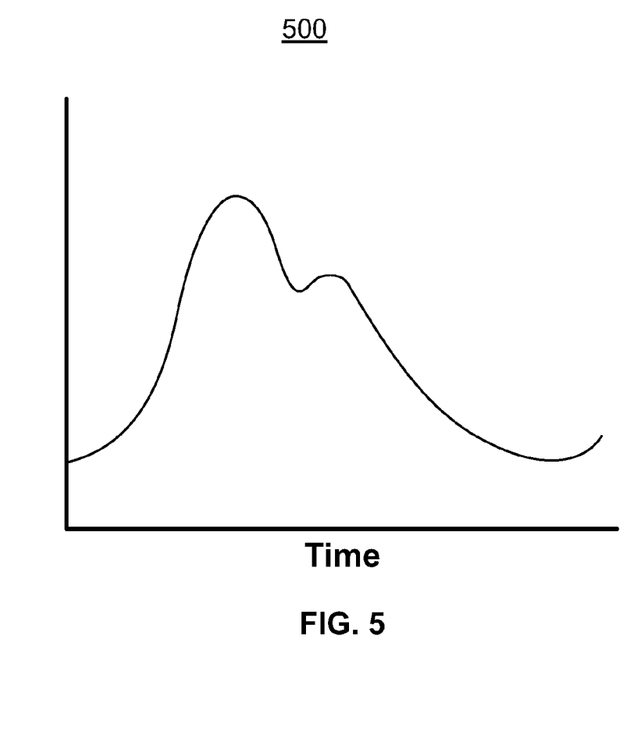
FIG. 5 shows an illustrative measured pulse waveform.

FIG. 5 shows a pulse waveform 500 measured using a pulse sensor, such as pulse sensor 120 discussed above with respect to FIG. 1. Pulse waveform 500 may be a trend of light received by a photosensor after transmission into the tissue from an LED. The percentage of light perceived is indicative of the volume of blood in the tissue, which is proportional to the pressure in the blood vessels and thus closely mirrors the trend measured by a pressure sensor. Because variations may be introduced into this measurement by elasticity differences in a subject's vessels, periodic calibration and correction based on the calibration data may be necessary to maintain the accuracy of pulse waveform 500. As is shown in FIG. 5, pulse waveform 500 has substantially the same shape over a single cardiac cycle as a typical blood pressure waveform, such as pressure waveform 200 in FIG. 2. In particular, the contours of the peak of the systolic phase and the dicrotic notch at the transition from systole to diastole have a substantially similar shape and occur at substantially the same temporal location within the pulse as corresponding points in pressure waveform 200.

A pressure waveform, such as pressure waveform 400 in FIG. 4, is measured at a subject's limb under applied constant pressure, and a pulse waveform, such as pulse waveform 500 in FIG. 5, is simultaneously measured at another location on the subject. The two measured waveforms are then combined to extrapolate the portions of the blood pressure waveform that are masked by the applied pressure and obtain complete blood pressure measurements. To obtain the extrapolated portions of the pressure trend, the two waveforms are first normalized and corrected based on calibration data, and then aligned according to one or more of the landmarks within the pulses of the waveforms. The masked sections of the normalized pressure waveform can then be filled in through extrapolation using the complete normalized pulse waveform as a template. The normalized, extrapolated pressure waveform may be processed to determine the subject's diastolic pressure that is initially masked by the constant applied pressure when pressure measurements are obtained.

A subject's pressure waveform and pulse waveform that are measured simultaneously, while exhibiting substantially the same general trend shape and temporal landmarks, may have different scaling that makes a direct correlation of the two waveforms difficult or impossible. Normalization can be used to facilitate the comparison of the two waveforms by eliminating any scaling differences and allowing for easier overlaying and extrapolation of the two waveforms.

Figure 6:
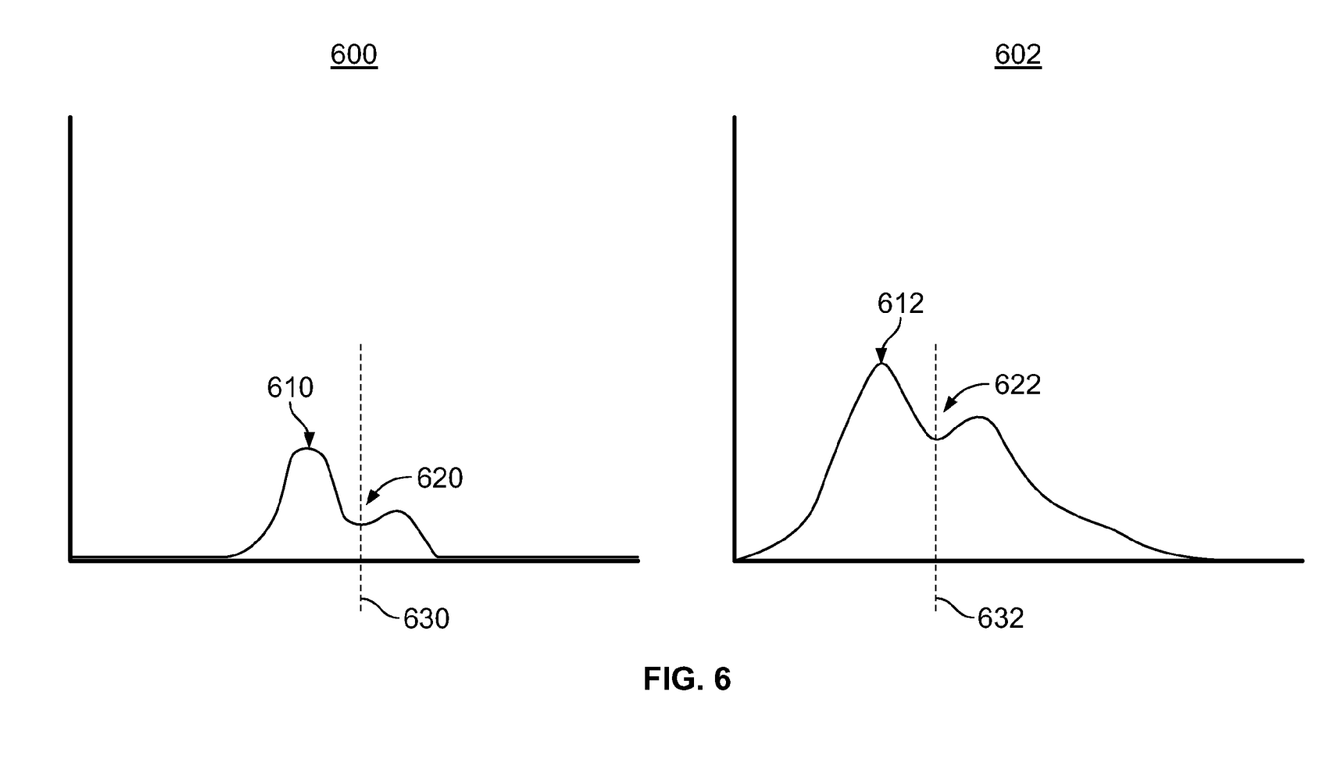
FIG. 6 shows an illustrative normalized pressure waveform and an illustrative normalized pulse waveform.

FIG. 6 shows normalized pressure waveform 600 and normalized pulse waveform 602, which may correspond, for example, to normalized forms of pressure waveform 400 in FIG. 4 and pulse waveform 500 in FIG. 5, respectively. While the two waveforms may have different scaling before normalization, it can be seen in FIG. 6 that the normalization eliminates the major differences caused by the scaling. Because the two original measured waveforms have different scaling, different normalization variables may be required for the pressure waveform than the pulse waveform. The pulse waveform may also be corrected based on calibration data to account for any changes or error introduced by inelasticity of a subject's blood vessels. As a result, the general geometries of the major portions of the trend are on substantially the same scale and exhibit substantially the same shape. For example, the shape of the portion of normalized pressure waveform 600 that includes systolic pressure 610 and the dicrotic notch 620 is substantially the same shape as the portion of normalized pulse waveform 602 that contains points 612 and 622, which correspond to the systolic peak and dicrotic notch of the cardiac cycle.

Due to the similarities in the geometry of the two normalized waveforms, the dicrotic notch of the cardiac cycle is clearly distinguishable at substantially the same time in each waveform. This is seen in timestamps 630 and 632 of the normalized waveforms 600 and 602, respectively. Timestamp 630 corresponds to the trough of the dicrotic notch 630, and timestamp 632 corresponds to the trough indicated by point 622 at the dicrotic notch of the cardiac cycle. The two timestamps 630 and 632 occur at substantially the same time (i.e., substantially the same position along the x-axis) within the pulse shown, and thus demonstrate the temporal correlation between the two normalized waveforms 600 and 602. The same relationship can be seen between the systolic peak points of the two normalized waveforms. Accordingly, the normalized waveforms 600 and 602 contain similar landmarks of the cardiac cycle that occur at substantially the same time with substantially the same shape in the two waveforms. This degree of correlation facilitates the alignment and overlaying of the two waveforms.

Figure 7:
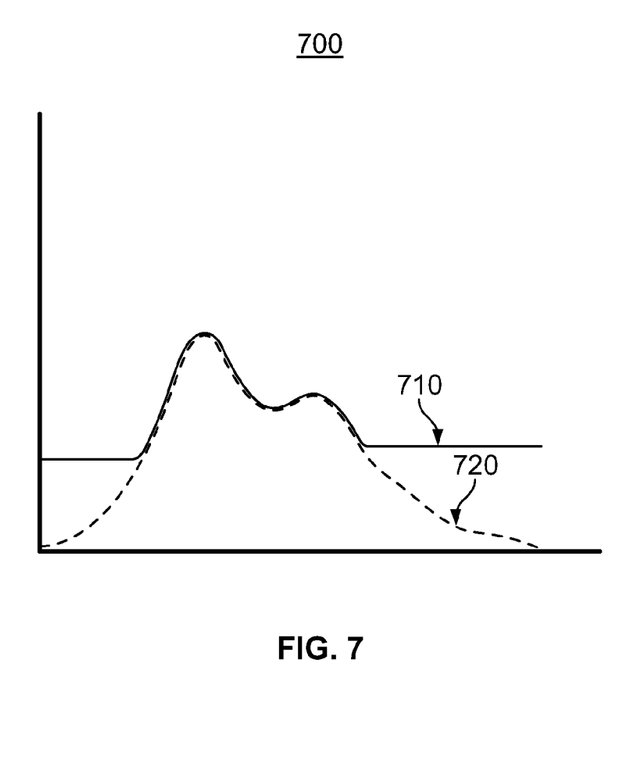
FIG. 7 shows an illustrative combined waveform.

FIG. 7 shows a combined waveform 700 in which a normalized pressure waveform 710, which may correspond to normalized pressure waveform 600 of FIG. 6, is overlaid with a normalized pulse waveform 720, which may also be corrected based on calibration data and may correspond to normalized pulse waveform 602 of FIG. 6. The similar geometries of the two normalized waveforms facilitates the overlaying, as the contours of the two trends generally correlate. Taking advantage of this correlation, the two waveforms can be overlaid by identifying and aligning the systolic peaks, dicrotic notches, or performing a combined alignment using both landmarks. The identification and alignment can be performed by any suitable process. In an embodiment, the waveforms are processed to detect maximum points within the pulses, which will generally correspond to the systolic peaks. The maximums in the pressure waveform correspond to maximums in the pulse waveform at substantially the same temporal locations, and the waveforms can be aligned based on these times. In an embodiment, the waveforms are processed to detect local minimum points within the pulses, which will generally correspond to the dicrotic notch. As with the systolic peaks, the waveforms can be aligned based on the times of the dicrotic notches. By using these landmarks, the pressure and pulse waveforms can still be overlaid when there are temporal differences between the pulse and pressure waveforms. For example, if a pressure sensor is located near the heart and a pulse sensor is located at a further peripheral location, the landmarks in the pulse waveform may be slightly delayed due to the time it takes for a pulse to travel through the circulatory system. By using the systolic and dicrotic landmarks, these small temporal differences can be accounted for and the pulses can still be accurately overlaid. A temporal range within a waveform, such as the time difference between the timepoint of the systolic landmark and the timepoint of the dicrotic landmark, may also be used for alignment. Additionally, any other consistent landmark in a subject's pulse waveform, whether common or specific to the subject's waveform, may be detected and used for alignment.

The overlaid waveforms in FIG. 7 demonstrate the utility of normalized pulse waveform 720 in extrapolating the portions of normalized pressure waveform 710 that are masked by the pressure applied to the subject. Due to the degree of correlation between the typical pulse and pressure waveforms, the tail ends of pulse waveform 720 for each pulse of the cardiac cycle provide an accurate estimation of the masked tail ends of the pressure waveform for each pulse. Normalized pulse waveform 720 is derived from a sensor that measures a different physiological parameter than the sensor from which normalized pressure waveform 710 is derived, and thus it cannot be used to directly determine the absolute values for the masked portions of normalized pressure waveform 710. Because both waveforms are normalized, the differences in scale and absolute values are eliminated, and the trend of normalized pulse waveform 720 can be used to extrapolate the general trend of the masked portions of normalized pressure waveform 710. From the extrapolated trend, the absolute pressure values of these portions of the pressure waveform can be subsequently determined.

Figure 8:
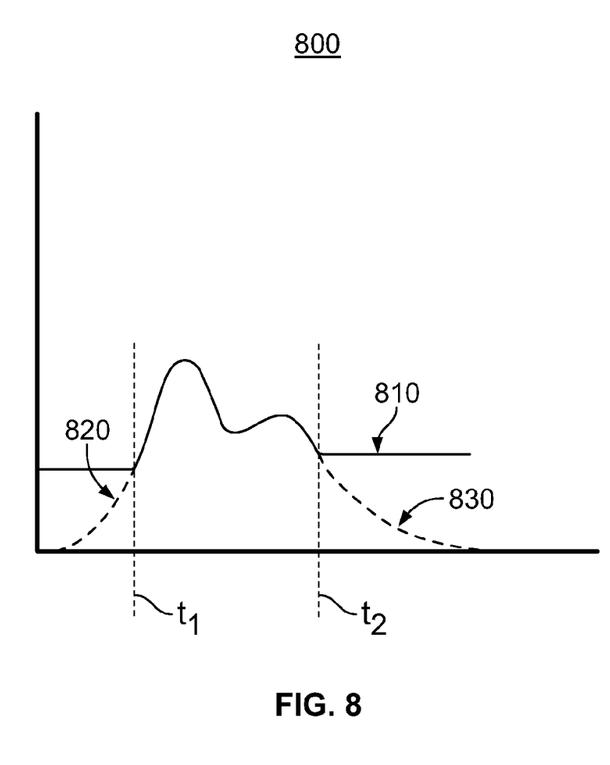
FIG. 8 shows an illustrative completed normalized pressure waveform.

FIG. 8 shows a completed normalized pressure waveform 800, which includes a normalized measured pressure waveform 810 with extrapolated tail portions 820 and 830. A representation of the subject's complete normalized blood pressure waveform is formed using tail portion 820 until time $t_1$, at which point the subject's blood pressure exceeds the applied pressure, using measured portion 840 from time $t_1$ to time $t_2$, at which point the subject's blood pressure falls back below the applied pressure, and using tail portion 830 for the remainder of the pulse. Through this processing, normalized pressure waveform 800 is transformed into a representation of a subject's full pulse. When multiple pulses are measured during blood pressure monitoring, a full representation of the subject's blood pressure trend is thus created as a continuous alternating cycle of (1) directly measured pressures and (2) extrapolated masked pressures.

The times $t_1$ and $t_2$ shown in FIG. 8 can be sensed for each pulse and used as triggers to alternate between using the directly measured pressures and the extrapolated masked pressures to create a subject's full blood pressure trend. In an embodiment, these timepoints in the trend can be detected by comparing the measured pressure value to the known constant pressure that is applied to the subject. In such an approach, the extrapolated pressures are used anytime the detected pressure is equal to the applied pressure, and the measured pressure is used anytime the detected pressure is greater than the applied pressure. In another embodiment, derivatives of measured pressure waveform 810 can be continuously calculated. During times when the measured pressure is equal to the constant applied pressure, both the first and second derivatives of measured pressure waveform 810 are equal to zero because the measured pressure is constant over time. During times when the measured pressure is greater than the applied pressure, at least one of the first and second derivatives is not equal to zero as a result of the fluctuating pressures seen between times $t_1$ and $t_2$. Thus, the full blood pressure trend can be created using the extrapolated pressures at times during which both the first and second derivatives are equal to zero and using the measured pressures at all other times.

Figure 9:
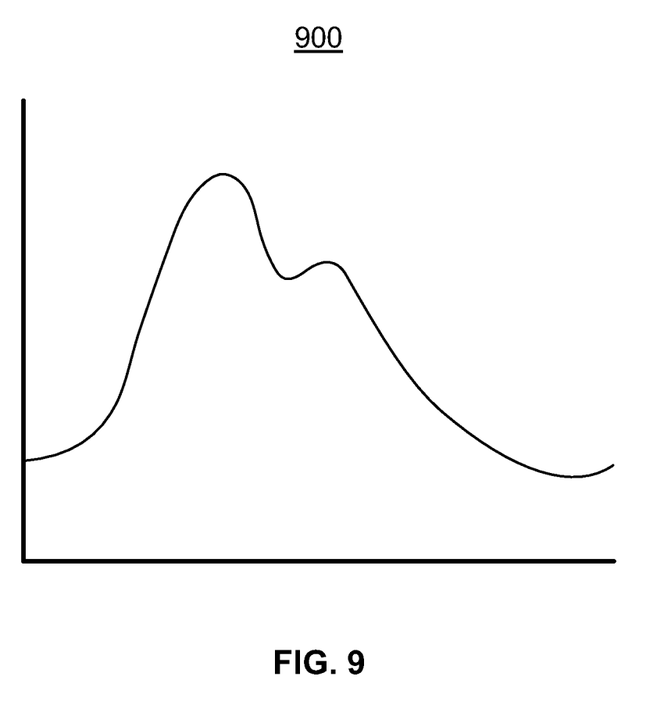
FIG. 9 shows an illustrative restored pressure waveform.

A completed normalized blood pressure waveform is restored to the scale of the original measured blood pressure waveform from which the normalized waveform is created to determine a subject's diastolic blood pressure. FIG. 9 shows a single pulse of a blood pressure waveform 900 restored to original scale. Although blood pressure waveform 900 includes portions that were extrapolated from a measured pulse waveform, the waveform is a full blood pressure trend with all of the landmarks of a typical subject's blood pressure trend, such as blood pressure waveform 200 discussed above in relation to FIG. 2. The extrapolated portions are taken from an original waveform, the pulse trend, that has different values and scaling than the original measured pressure waveform. The extrapolated portions are normalized using the normalization variables for the pulse waveform and are restored suing the normalization variables for the pressure waveform, which are likely to be different due to the different scaling, as discussed above in relation to FIG. 6. Because the shape of the extrapolated portions in the original pulse waveform are substantially similar to analogous portions of the subject's blood pressure waveform which are masked by the applied pressure, these portions of the restored pressure waveform 900 are an accurate estimation of the masked pressures. The subject's diastolic pressure, which is within the range of masked pressures, can thus be determined by simply determining the minimum pressure within a pulse of pressure waveform 900.

Using the applied constant pressure and measurements techniques, accurate blood pressure measurements are continuously obtained from a subject. A subject's systolic and diastolic pressure can be obtained from a single pulse. This resolution is not possible with traditional blood pressure measurement techniques, which require multiple pulses to take a single reading of systolic and diastolic pressure. Accordingly, the systems and methods described herein may detect acute increases or decreases in the subject's blood pressure more efficiently than other standard techniques.

Pressure measurements from multiple successive pulses may also be used in calculating a subject's systolic and diastolic blood pressures in an embodiment of the invention. For example, the systolic and diastolic measurements from multiple successive pulses may be averaged to obtain a single reading of the two pressures for the subject. In an embodiment, the average may be computed using a sliding window of a set number of previous pressure measurements. The size of the sliding window used may be constant, or may change based on the measurements obtained. In an embodiment, the size of the sliding window may be set by user input. For example, a user may select a large window for continuous patient monitoring when little change in blood pressure is expected, or the user may select a short window for acute monitoring to detect subtle changes during spurts of physical exertion.

The blood pressure measurements obtained during monitoring of a subject may be combined or correlated with other physiological measurements in some applications of the invention. Other measurements that may be useful to evaluate are heart rate, temperature, breathing rate, electrocardiogram, electromyogram, or any other suitable measurement. The comparison can be used to monitor changes in a subject's blood pressure during periods of stress or physical exertion, such as an interval training routine that includes alternating cycles of high and low intensity exertion. During an interval training routine, a subject's blood pressure can be combined with a measure indicative of the level of exertion, such as heart rate, to identify blood pressure trends related to the exertion and relaxation periods. In an embodiment, baseline blood pressure readings are obtained, and deviations from this baseline during periods of physical exertion, as determined from a heart rate reading, are calculated to quantify the effect of the exertion on the subject's blood pressure. Depending on the physiological measurements used and the specific monitoring application, aspects of the measurement technique, such as a sliding averaging window, can be adjusted for optimal accuracy. For example, in acute applications, such as interval training, this window may be narrower than usual to allow for more accurate detection of acute increases or decreases in blood pressure.

During monitoring of a subject, periodic calibration may be performed automatically to ensure accuracy of the blood pressure data obtained. The calibration may be run to detect unwanted nonlinearities in the data or to optimize the magnitude of the constant pressure applied to the subject. In an embodiment, calibration is performed at the beginning of subject monitoring to ensure accurate measurements are obtained. During continuous measurement, the calibration may be performed periodically to ensure accuracy is maintained and detect any needed adjustments, such as changing the constant pressure applied to the subject. Nonlinearities in the obtained measurements or irregular systolic and diastolic pressure measurements may be used as indicators that adjustments are needed. The frequency of calibration may be a set frequency, or may change dynamically based on previous calibrations and the measurements obtained. In an embodiment, it is preferable to calibrate the measurement system only as often as is necessary to maintain data accuracy. For a subject whose blood pressure is not changing, this frequency may be less often than a subject whose blood pressure is exhibiting frequent fluctuations. Based on the stability of pressure measurements made and the amount of time since adjustments were last made, a system of the invention may increase or decrease the frequency of calibration cycles. In an embodiment, a calibration cycle may be run only in response to user input starting the calibration.

Figure 10:
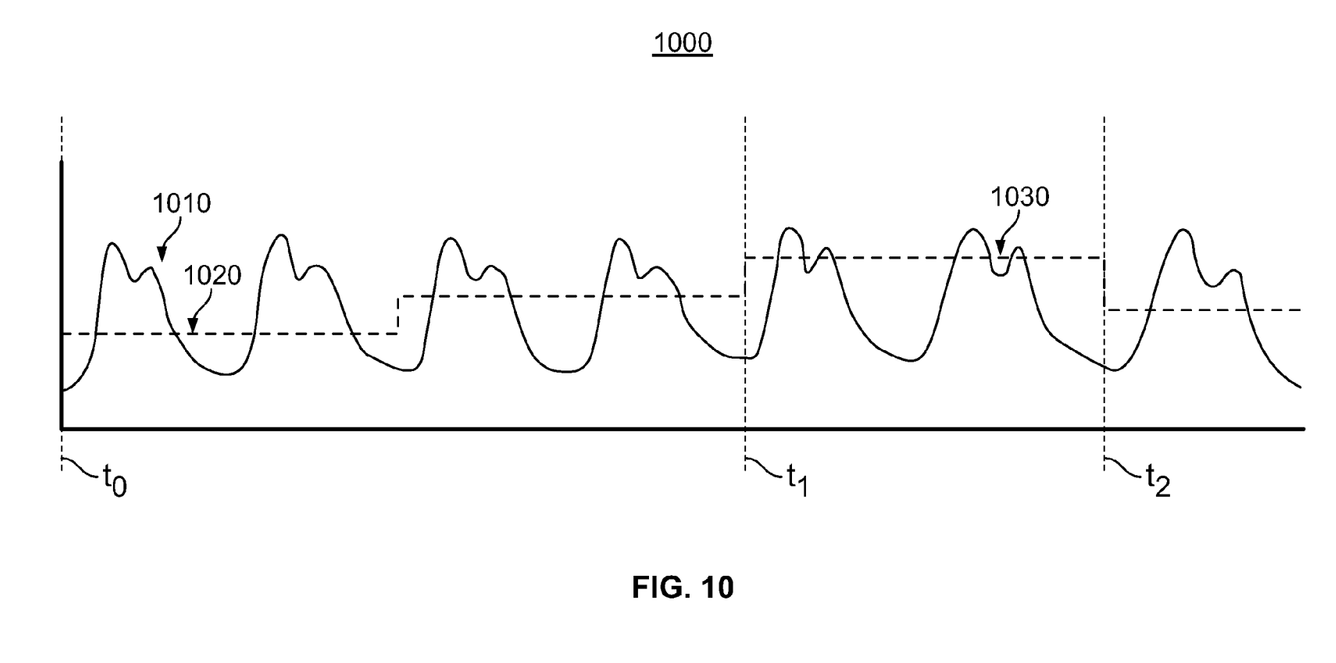
FIG. 10 shows an illustrative calibration cycle.

An example of a calibration cycle 1000 is shown in FIG. 10. The calibration cycle shown is used to select a constant pressure to be applied to a subject to obtain blood pressure measurements. The subject's actual blood pressure trend 1010 is shown along with applied pressure 1020 that is used during calibration. Calibration begins at time $t_0$, and a low pressure is chosen for applied pressure 1020 to ensure that the starting calibration pressure is below the key landmarks, the systolic pressure and the pressure at the dicrotic notch, in the subject's pressure trend 1010. The starting calibration pressure may be a set value for each calibration round or, in some embodiments, may be set simply as the subject's measured diastolic pressure preceding the calibration.

During calibration, the magnitude of the constant applied pressure is incrementally increased, and pressure measurements are taken at each incremental pressure level. The applied pressure may be increased after each measured pulse, or may be incremented such that more than one pulse is measured at each pressure step, as shown in FIG. 10. Though not strictly necessary, at least one full pulse is preferably measured at each pressure step. For each pressure step, incident pressure is measured as in standard subject monitoring, and the systolic and dicrotic landmarks are identified for each discernible pulse. Eventually, the applied pressure is increased to a pressure greater than the pressure at the dicrotic pressure, as shown at time $t_1$. The measurements taken for subsequent pulses include systolic peak measurements but no discernible dicrotic notch, as this pressure is now masked by the applied pressure. A determination is made that the dicrotic landmark is no longer measurable, for example, by detecting irregularities in the timing of measurements that are equal to the applied pressure, for example, at segment 1030 of the calibration cycle. Once the pressure that exceeds the pressure at the dicrotic notch is determined, this value and measurements taken at previous pressure steps are used to determine a suitable applied pressure to be used for subject monitoring. At time $t_2$, the calibration cycle ends, and the applied pressure is set to the determined suitable pressure for normal blood pressure monitoring during subsequent pulses.

The calibration process shown in calibration cycle 1000 may also be performed to update calibration data used to adapt to any nonlinearities in readings caused by inelasticity of a subject's tissue. The nonlinearities may be present from the beginning of blood pressure measurement, or may be gradually introduced as continuous blood pressure measurements and calibrations are performed. For example, inelastic properties of the subject's vessels may cause the nonlinearities to increase as constant pressure is applied to the subject and subsequent calibration cycles are performed. By updating the calibration data based on the detection of these nonlinearities, the potential error can be eliminated, and subsequent readings following calibration can be corrected to maintain measurement accuracy.

Figure 11:
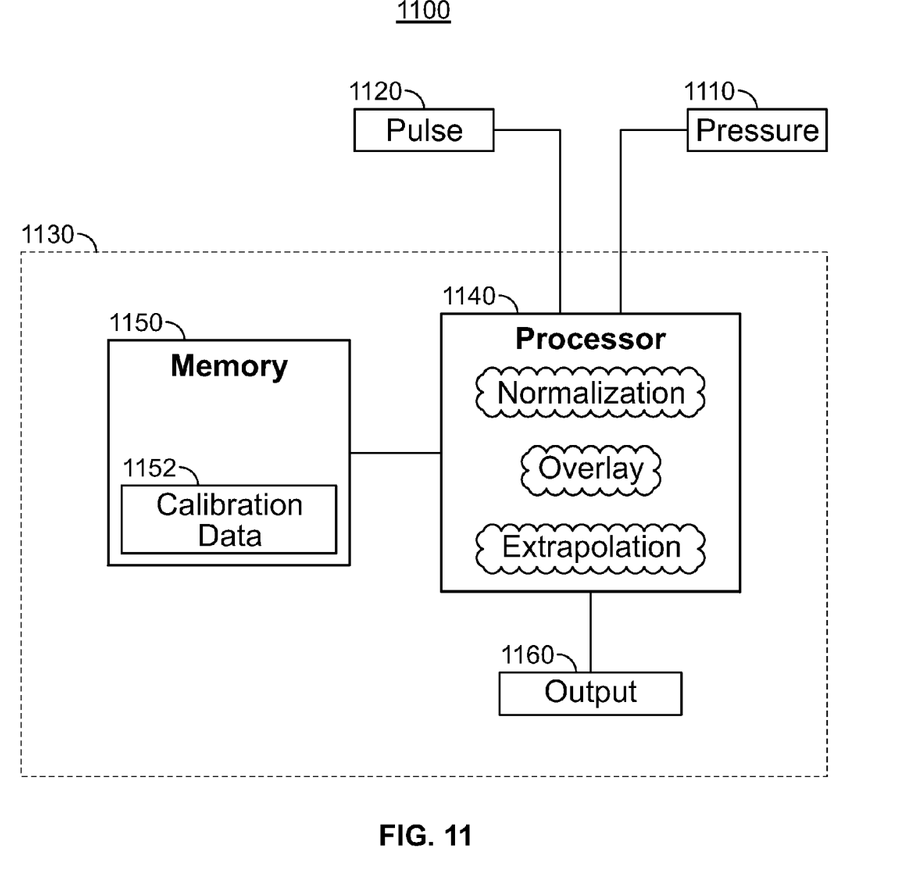
FIG. 11 shows an illustrative measurement device.

FIG. 11 shows an illustrative measuring device 1100 for obtaining blood pressure measurements for a subject. Measuring device 1100 includes a pressure sensor 1110, pulse sensor 1120, and processing module 1130. Pressure sensor 1110 is configured to apply a constant pressure to the subject and obtain pressure measurements, and may have substantially the same function as pressure sensor 110 discussed above in relation to FIG. 1. Pulse sensor 1120 is configured to monitor a patient's pulse, and may have substantially the same function as pulse sensor 120 discussed above in relation to FIG. 2.

Processing module 1130, which includes processor 1140, memory 1150, and data output 1160, is in communication with pressure sensor 1110 and pulse sensor 1120. The sensors may communicate with processing module 1130 wirelessly, or may communicate with processing module 1130 via a wired connection. Signals obtained from the sensors are passed to processor 1140 for data processing. Processor 1140 is configured to process the pressure and pulse readings using the method of the present invention to obtain systolic and diastolic pressure readings for the subject. For example, processor 1140 may be configured to perform normalization, overlaying, and extrapolation using waveforms obtained from the sensors to directly measure the subject's systolic blood pressure and determine the subject's diastolic pressure from the extrapolation, as described in the foregoing discussion.

Processor 1140 is also in communication with memory 1150. Memory 1150 may be used to store data for a subject. Data saved in memory 1150 may include raw data obtained from pressure sensor 1110 and pulse sensor 1120, systolic and diastolic pressure data determined by processor 1140, subject identification data, data indicating the constant pressure applied to the subject, or any other suitable data. Memory 1150 may also be used to store variables and information related to calibration of measurement device 1100.

Data and information is output by measurement device 1100 via data output 1160. Data output 1160 may support both wireless and wired communication with any receiving devices. Receiving devices may include a monitor, computer, handheld device, sensor hub, or any other suitable device. The data sent from measurement device 1100 may include any data obtained by processor 1140 or stored in memory 1150, such as systolic and diastolic pressure readings, patient identification data, raw data from sensors 1110 and 1120, the amount of pressure applied by pressure sensor 1110, calibration data, or any other suitable data.

The invention may be embodied in other specific forms without departing from the spirit or essential characteristics thereof. The foregoing embodiments are therefore to be considered in all respects illustrative, rather than limiting of the invention.

What is claimed is:

1. A method for blood pressure monitoring, comprising:
    applying a first measuring element to a subject for creating a constant pressure applied to the subject and monitoring pressure that exceeds the applied constant pressure;
    incrementally increasing the pressure applied by the first measuring element;
    monitoring the pressure that exceeds the increasing applied pressure;
    determining an applied pressure that is greater than a dicrotic pressure;
    based on the determination, setting the applied pressure for patient monitoring, wherein the set applied pressure is less than the determined pressure;
    applying a second measuring element to the subject for monitoring the subject's pulse;
    measuring, using the first measuring element, the subject's systolic blood pressure; and
    determining, based on the pressure monitored by the first measuring element and the pulse monitored by the second measuring element, the subject's diastolic blood pressure.

2. The method of claim 1, further comprising disposing the first measuring element at a location external to the body of the subject.

3. The method of claim 1, wherein the constant pressure applied by the first measuring element is less than the subject's systolic blood pressure.

4. The method of claim 1, further comprising determining the systolic blood pressure and the diastolic blood pressure from pressure and pulse measurements taken over a single cardiac cycle.

5. The method of claim 1, wherein a pressure waveform monitored by the first measuring element includes at least one masked portion during which the subject's blood pressure is not measured directly by the first measuring element.

6. The method of claim 5, further comprising:
    normalizing the pressure waveform monitored by the first measuring element and a pulse waveform monitored by the second measuring element;
    overlaying the normalized pressure waveform and the normalized pulse waveform; and
    determining the subject's diastolic blood pressure based on the overlaid waveforms.

7. The method of claim 6, wherein the normalized waveforms are overlaid by aligning a landmark in the waveforms.

8. The method of claim 7, wherein the landmark is the dicrotic notch.

9. The method of claim 7, wherein the landmark is the systolic peak.

10. The method of claim 7, wherein the landmark is the temporal difference between the systolic peak and the dicrotic notch.

11. The method of claim 6, further comprising extrapolating pressure values for the masked portions of the pressure waveform using a waveform trend of corresponding portions of the pulse waveform measured by the second measuring element.

12. The method of claim 5, further comprising correcting the pulse waveform using stored calibration data.

13. The method of claim 1, further comprising calculating, as a function of pressures measured at the first measuring element, the constant pressure to be applied to the subject.

14. The method of claim 13, wherein the constant pressure is calculated as a function of at least one of the systolic, diastolic, and dicrotic blood pressures of the subject.

15. The method of claim 1, further comprising averaging measured systolic blood pressures and determined diastolic blood pressures over multiple pulses to obtain a single value for each of the subject's systolic and diastolic blood pressures.

16. The method of claim 15, further comprising calculating a deviation from the averaged systolic and diastolic blood pressures for a blood pressure measurement taken from a single cardiac cycle, wherein the systolic and diastolic blood pressures are averaged over a sliding window of pulses.

17. The method of claim 16, further comprising comparing the calculated deviation to a heart rate.

18. The method of claim 1, further comprising periodically calibrating the first measuring element.

19. The method of claim 18, wherein the periodic calibration comprises:
    increasing the pressure applied by the first measuring element;
    monitoring the pressure that exceeds the increasing applied pressure;
    measuring, based on the monitored pressure, the systolic blood pressure of the subject;
    determining that nonlinearities are present in consecutive measurements taken at a single applied pressure; and
    updating stored calibration data based on the detected nonlinearities.

20. A system for blood pressure monitoring, comprising:
    a first measuring element for creating a constant pressure applied to a subject and monitoring pressure that exceeds the applied pressure;
    a second measuring element for monitoring the subject's pulse; and
    a processor in communication with the first and second measuring elements and configured to:
        incrementally increase the pressure applied by the first measuring element;
        monitor the pressure that exceeds the increasing applied pressure;
        determine an applied pressure that is greater than the dicrotic pressure; and
        based on the determination, set the applied pressure for patient monitoring, wherein the set applied pressure is less than the determined pressure;
        measure the subject's systolic blood pressure; and determine, based on the pressure monitored by the first measuring element and the pulse monitored by the second measuring element, the subject's diastolic blood pressure.

21. The system of claim 20, wherein the first measuring element is disposed at a location external to the body of the subject.

22. The system of claim 20, wherein the constant pressure applied by the first measuring element is less than the systolic blood pressure of the subject.

23. The system of claim 20, wherein the processor is further configured to determine the systolic blood pressure and the diastolic blood pressure from pressure and pulse measurements taken over a single cardiac cycle.

24. The system of claim 20, wherein a pressure waveform monitored by the first measuring element includes at least one masked portion during which the subject's blood pressure is not measured directly by the first measuring element.

25. The system of claim 23, wherein the processor is further configured to:
   normalize the pressure waveform monitored by the first measuring element and a pulse waveform monitored by the second measuring element;
   overlay the normalized pressure waveform and the normalized pulse waveform; and
   determine the diastolic blood pressure based on the overlaid waveforms.

26. The system of claim 25, wherein the processor is further configured to overlay the normalized waveforms by aligning a landmark point in the waveforms.

27. The system of claim 26, wherein the landmark point is the dicrotic notch.

28. The system of claim 26, wherein the landmark point is the systolic peak.

29. The system of claim 26, wherein the landmark is the temporal difference between the systolic peak and the dicrotic notch.

30. The system of claim 25, wherein the processor is further configured to extrapolate pressure values for the masked portions of the pressure waveform using a waveform trend of corresponding portions of the pulse waveform measured by the second measuring element.

31. The system of claim 25, wherein he processor is further configured to correct the pulse waveform using stored calibration data.

32. The system of claim 20, wherein the processor is further configured to calculate, as a function of pressures measured at the first measuring element, the constant pressure to be applied to the subject.

33. The system of claim 32, wherein the processor is further configured to calculate the constant pressure as a function of at least one of the systolic, diastolic, and dicrotic blood pressures of the subject.

34. The system of claim 20, wherein the processor is further configured to average measured systolic blood pressures and determined diastolic blood pressures over multiple pulses to obtain a single value for each of the subject's systolic and diastolic blood pressures.

35. The system of claim 34, wherein the processor is further configured to calculate a deviation from the averaged systolic and diastolic blood pressures for a blood pressure measurement taken from a single cardiac cycle, wherein the systolic and diastolic blood pressures are averaged over a sliding window of pulses.

36. The system of claim 35, wherein the processor is further comprised to compare the determined deviation to a heart rate.

37. The system of claim 21, wherein the processor is further configured to perform periodic calibration of the first measuring element.

38. The system of claim 36, wherein the periodic calibration comprises:
   increasing the pressure applied by the first measuring element;
   monitoring the pressure that exceeds the increasing applied pressure;
   measuring, based on the monitored pressure, the systolic blood pressure of the subject; and
   determining whether nonlinearities are present in consecutive measurements taken at a single applied pressure.

* * * * *